United States Patent
Forsyth (10) Patent No.: US 7,265,846 B2
(45) Date of Patent: Sep. 4, 2007

(54) METHODS FOR DETECTING ICE AND LIQUID WATER ON SURFACES

(75) Inventor: Keith W. Forsyth, Philadelphia, PA (US)

(73) Assignee: Sensors Unlimited, Inc., Princeton, NJ (US)

( * ) Notice: Subject to any disclaimer, the term of this patent is extended or adjusted under 35 U.S.C. 154(b) by 314 days.

(21) Appl. No.: 10/770,854

(22) Filed: Feb. 3, 2004

(65) Prior Publication Data

US 2005/0167593 A1    Aug. 4, 2005

(51) Int. Cl.
  *G01N 21/55* (2006.01)
  *G08B 19/02* (2006.01)
  *G01J 5/02* (2006.01)
(52) U.S. Cl. .................. 356/445; 340/583; 250/339.11
(58) Field of Classification Search ...................... None
  See application file for complete search history.

(56) References Cited

U.S. PATENT DOCUMENTS

| | | | | |
|---|---|---|---|---|
| 4,808,824 A | * | 2/1989 | Sinnar ................... | 250/339.11 |
| 5,180,122 A | * | 1/1993 | Christian et al. ........ | 244/134 F |
| 5,218,206 A | | 6/1993 | Schmitt et al. ............ | 250/339 |
| 5,500,530 A | * | 3/1996 | Gregoris ................ | 250/339.11 |
| 5,596,320 A | * | 1/1997 | Barnes ........................ | 340/962 |
| 5,818,339 A | * | 10/1998 | Giles et al. .................. | 340/583 |
| 5,921,501 A | * | 7/1999 | Pernick .................... | 244/134 F |
| 6,049,387 A | * | 4/2000 | Griesinger .................. | 356/419 |
| 6,166,645 A | * | 12/2000 | Blaney ........................ | 340/583 |

\* cited by examiner

*Primary Examiner*—Michael P. Stafira
(74) *Attorney, Agent, or Firm*—McCarter & English, LLP

(57) ABSTRACT

Methods for detecting the presence or absence of ice or liquid water on surfaces are provided. In a first embodiment of the invention, a reflectance spectrum from a surface to be tested is measured using any suitable near-infrared optical system. The midpoint wavelength of the transition or step of the measured reflectance spectrum near 1.4 microns is calculated, and compared to a decision threshold wavelength. If the midpoint wavelength is less than the decision threshold wavelength, the presence of liquid water on the surface is indicated. If the midpoint wavelength is greater than the decision threshold wavelength, the presence of ice is indicated on the surface. In a second embodiment of the invention, at least three reflectance levels are measured at three wavelengths, and a dimensionless decision function is applied to the measured reflectance levels. Output of the decision function is compared to at least two pre-defined ranges. If the output is within a first range, the presence of liquid water on the surface is indicated. If the output is within a second range, the presence of ice on the surface is indicated. If the output is between the pre-defined ranges, the absence of ice or water on the surface is indicated.

56 Claims, 4 Drawing Sheets

METHODS FOR DETECTING ICE AND LIQUID WATER ON SURFACES

BACKGROUND OF THE INVENTION

1. Field of the Invention

The present invention relates to the detection of ice and liquid water on surfaces. More specifically, the present invention relates to methods for detecting ice and liquid water on surfaces using optical reflectance and wavelength shift analysis.

2. Related Art

The presence of ice on surfaces can present a number of hazards. For example, when ice accumulates on aircraft surfaces and runways, air travel safety is jeopardized. Additionally, the presence of ice on roadway surfaces increases the risk of losing control, thus leading to dangerous driving conditions. Detecting ice on surfaces is therefore desirable, so that such dangerous conditions can be identified and avoided. However, the detection of ice on wet surfaces is difficult, particularly when ice forms in a thin sheet at temperatures near the freezing point of water. Therefore, what is needed is a non-contact method for automatically discriminating between liquid water and solid ice on surfaces.

The optical reflectance spectra of ice and liquid water can be analyzed to detect the presence or absence of ice or liquid water on surfaces, without requiring physical contact with the surface. The optical reflectance spectra of both liquid water and solid ice have a number of distinguishing features, particularly within the near-infrared portion of the spectrum. Most of these features originate from the absorption characteristics of the O—H covalent bond within each ice or water molecule. Since the strength of the covalent bond varies with the strength of the hydrogen bonds between water molecules, the properties of the absorption bands vary with temperature and entropy. This variation in spectral properties is particularly large when water undergoes a phase transition between the liquid and solid states, and is detectable using optical equipment and spectral monitoring techniques.

The characteristics of the absorption band centered near a wavelength of 1.45 microns can be analyzed to discriminate between liquid water and solid ice on a surface. This absorption band is identified in the spectroscopic literature as being caused by the first overtone combination of the symmetric and asymmetric vibrational stretching modes of the O—H covalent bond of water molecules. The short-wavelength edge of this absorption band located near a wavelength of 1.4 microns shifts from a shorter to a longer wavelength by approximately 40 to 50 nanometers when a thin layer of liquid water at a temperature near zero degrees Celsius freezes into ice. This wavelength shift can be analyzed to determine the presence of ice on surfaces.

Various systems have been developed for detecting ice on surfaces. Optical ice detection systems have been developed wherein the optical reflectance of ice is measured in narrow bands centered at specific wavelengths in the near-infrared portion of the optical spectrum. However, such optical systems distinguish the presence of liquid water from ice using only the ratio of the reflectance magnitudes in two specified wavelength bands, wherein certain reflectance ratios indicate the presence of liquid water and other ratios indicate the presence of ice. However, such systems have poor reliability when ice is thin (e.g., approximately 1 mm or less), and cannot effectively compensate for system noise and changes in ambient light.

Accordingly, what would be desirable, but has not heretofore been provided, are robust methods for detecting the presence of water and ice on surfaces using optical spectral analysis of absorption bands in the near-infrared region.

SUMMARY OF THE INVENTION

The present invention relates to methods for detecting the presence of ice or liquid water on surfaces. A reflectance spectrum is acquired from a surface to be analyzed using any suitable optical apparatus. The transition or step in the reflectance spectrum corresponding with the short-wavelength edge of the absorption band near 1.4 micrometers is identified, and the midpoint wavelength of the transition is calculated. The calculated midpoint wavelength is compared to a decision threshold wavelength. If the measured midpoint wavelength is less than the decision threshold wavelength, a downward wavelength shift of the absorption band is detected, and an indication that liquid water is present on the surface is generated. If the measured midpoint wavelength is greater than the decision threshold wavelength, an upward wavelength shift of the absorption band is detected, and an indication that ice is present on the surface is generated. Variations in surface properties, illumination levels, instrument noise, instrument offsets, ice or water thicknesses, and other variations, can be compensated for by the method of the present invention.

In an embodiment of the present invention, a method for determining the presence or absence of ice or liquid water on a surface is provided. At least three reflectance levels are measured from the surface at three pre-determined wavelengths near the 1.4 micron absorption band edge. A decision function is applied to the measured reflectance levels, and represents a dimensionless function or mapping of the midpoint wavelength of the reflectance transition that can be readily calculated. At least two pre-determined numerical ranges are retrieved, and the result of the decision function is compared to the ranges. If the result is within the first pre-determined range, an indication is generated that liquid water is present on the surface. If the result is within a second pre-determined range, an indication is generated that ice is present on the surface. If the result is between the ranges, an indication is generated that neither ice nor liquid water is present on the surface.

BRIEF DESCRIPTION OF THE DRAWINGS

These and other important objects and features of the invention will be apparent from the following Detailed Description of the Invention, taken in connection with the accompanying drawings, in which.

DETAILED DESCRIPTION OF THE INVENTION

The present invention relates to methods for detecting the presence of ice or water on surfaces. According to one method of the present invention, a reflectance spectrum from a surface to be tested is measured using any suitable near-infrared optical system. The midpoint wavelength of the reflectance magnitude transition near 1.4 microns is calculated, and compared to a decision threshold wavelength. If the midpoint wavelength is less than the decision threshold wavelength, the presence of liquid water on the surface is indicated. If the midpoint wavelength is greater than the decision threshold wavelength, the presence of ice is indicated on the surface.

According to another method of the invention, at least three reflectance levels are measured at three wavelengths, and a decision function is applied to the measured reflectance levels. The dimensionless output of the decision function is compared to at least two pre-defined ranges. If the output is within a first range, the presence of liquid water on the surface is indicated. If the output is within a second range, the presence of ice on the surface is indicated. If the output is between the ranges, the absence of ice or liquid water on the surface is indicated.

Figure 1:
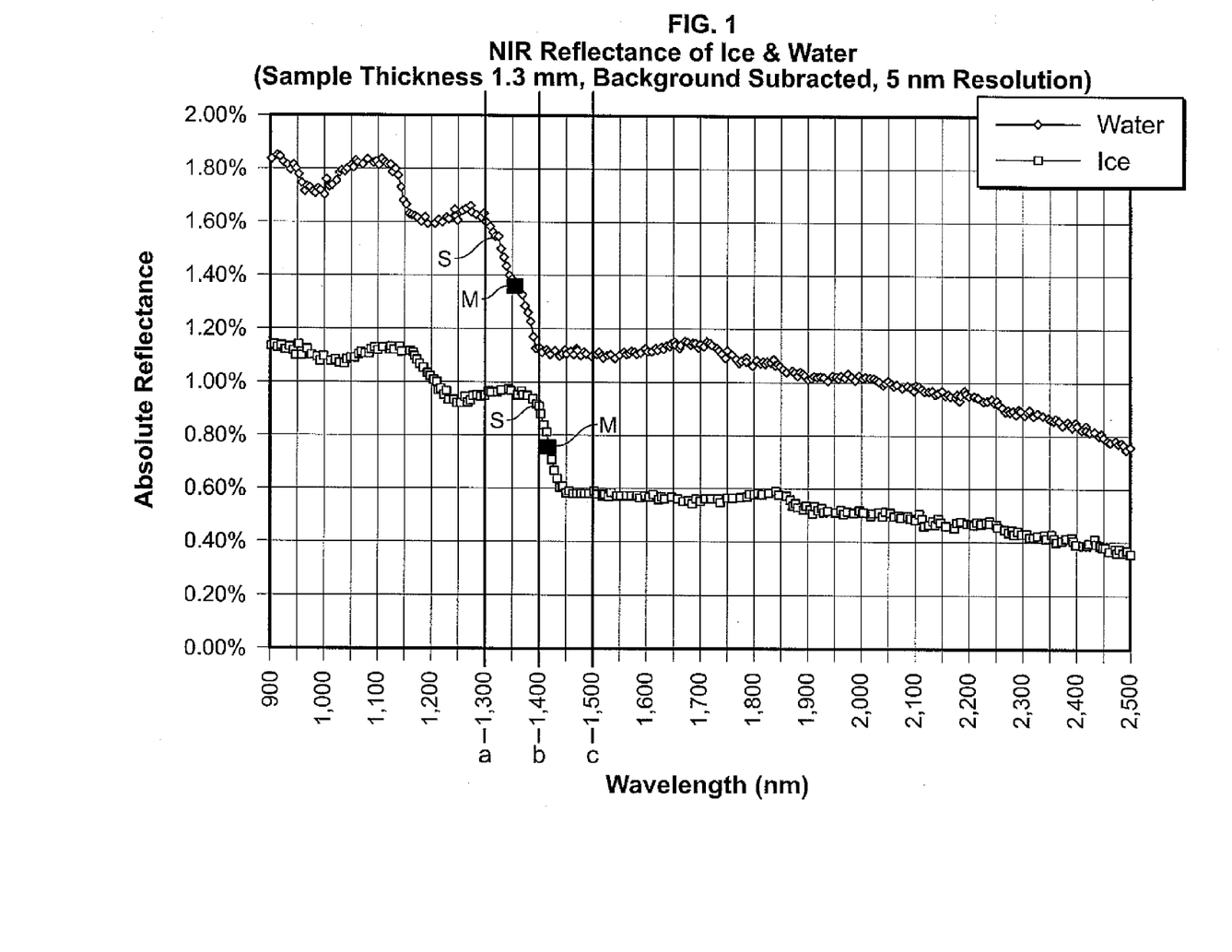
FIG. 1 is a graph showing near-infrared reflectance spectra of ice and liquid water on a sample surface, and three sample wavelengths at which reflectance measurements are made by the present invention.

FIG. 1 is a graph showing near-infrared reflectance spectra of ice and liquid water on a sample surface. In each spectrum, a transition or "step" in the reflectance magnitude, indicative of an absorption band edge and indicated in FIG. 1 as step S, is present near a wavelength of 1.4 micrometers. The step S occurs as a result of the first overtone combination of the symmetric and asymmetric vibrational stretching modes of the O—H covalent bond within ice or liquid water molecules present on the surface. The position of the step S in each spectrum varies according to whether the water molecules are solid (i.e., ice is present on the surface), or liquid (i.e., liquid water is present on the surface). In the case of liquid water, the step S shifts toward shorter wavelengths, as show in the upper spectrum in the graph shown of FIG. 1. In the case of ice, the step S shifts toward longer wavelengths, as shown in the lower spectrum. The midpoint M of each step S can be calculated and compared to a decision threshold wavelength to determine the presence or absence of ice on a surface.

A preferred decision threshold wavelength corresponds to a wavelength of approximately 1.4 microns, and is shown as wavelength b in FIG. 1. If the calculated midpoint M has a shorter wavelength than approximately 1.4 microns, as shown in the upper graph of FIG. 1, then liquid water is present on the surface. Conversely, if the calculated midpoint M has a longer wavelength than approximately 1.4 microns, as shown in the lower graph of FIG. 1, then ice is present on the surface. It should be noted that the exact decision threshold wavelength can vary slightly (i.e., approximately+/−0.05 microns) with a particular application, as well as with fluctuations in the expected thickness of the liquid water or ice layer, the expected temperature range, and the details of the construction of the optical measurement apparatus.

In one embodiment of the present invention, reflectance levels at three wavelengths a, b, and c, centered at approximately 1.3, 1.4, and 1.5 microns, respectively, can be detected, and a decision function applied to the three reflectance levels. The output of the decision function can then be compared to pre-determined thresholds to determine the presence or absence of liquid water or ice on a surface.

Figure 2:
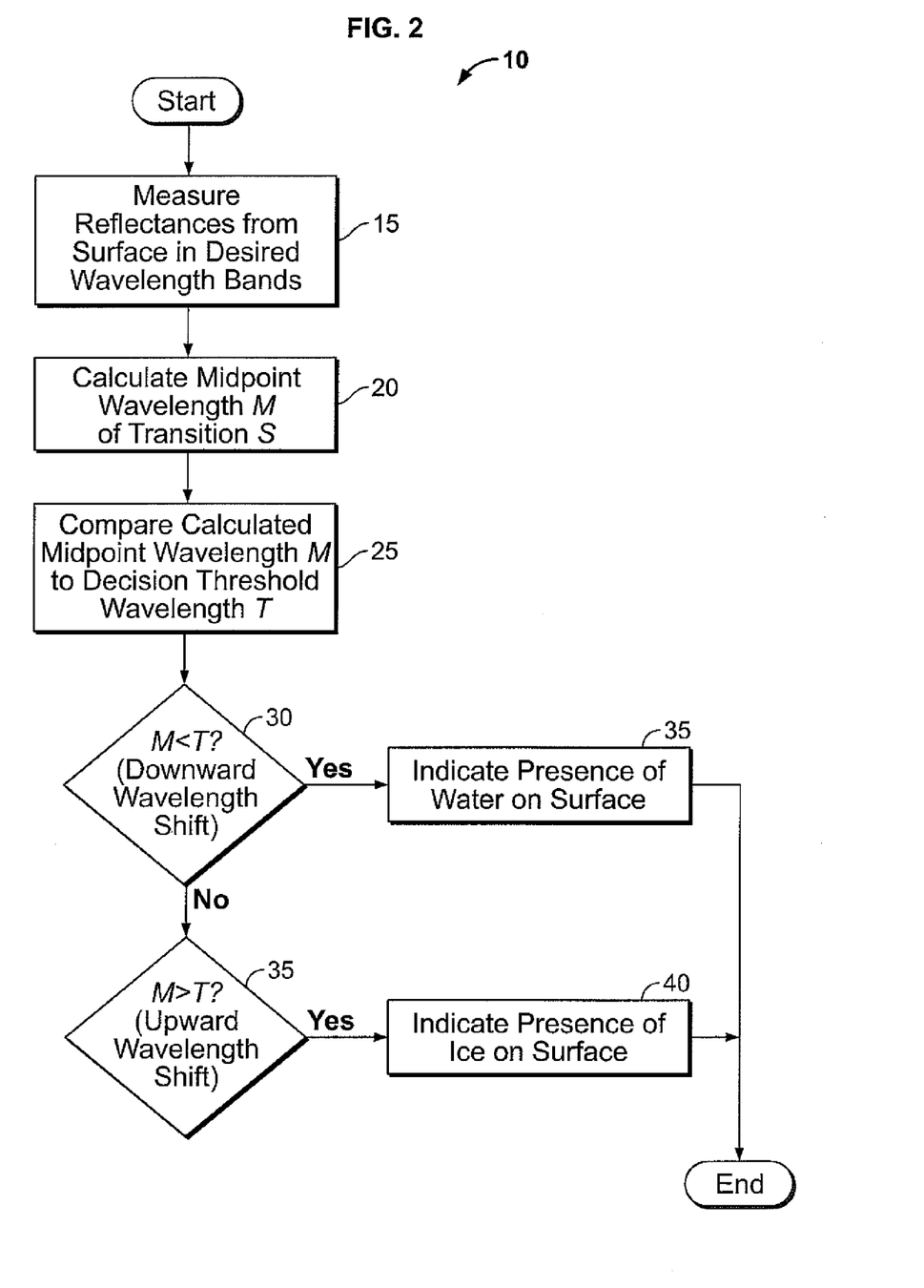
FIG. 2 is a flowchart showing the method of the present invention for determining the presence of water or ice on a surface.

FIG. 2 is a flowchart showing a method according to the present invention for detecting ice or liquid water on surfaces, indicated generally at 10. Beginning in step 15, reflectance from a surface to be tested is measured in a plurality of wavelength bands, and a reflectance spectrum is generated. Any known system for measuring surface reflectance can be utilized, such as an InGaAs focal plane array camera, PbS vidicon, or other suitable detector and associated circuitry. In step 20, the midpoint wavelength M of the step S (such as the steps shown in FIG. 1 and discussed earlier) is calculated. Then, in step 25, the calculated midpoint wavelength M is compared to a decision threshold wavelength T to determine whether ice or liquid water is present on the surface. Threshold T is preferably near 1.4 microns, but could be altered slightly to account for wavelength shifts attributable to ambient or surface temperatures, expected ice or liquid water layer thicknesses, or instrumental effects.

In step 30, a determination is made as to whether the calculated midpoint wavelength M is less than the threshold wavelength T. If a positive determination is made, a downward wavelength shift is detected, corresponding to the presence of liquid water on the surface. Step 35 is then invoked, wherein the presence of liquid water on the surface is indicated. Such an indication could be in any desired format, such as by activating one or more indicators on a device (audio, visual, etc.), sending a message to a computer terminal or across a network, or in any other fashion. In the event that a negative determination is made in step 30, step 35 is invoked, wherein a determination is made as to whether the midpoint wavelength M is greater than the threshold wavelength T. If a positive determination is made, an upward wavelength shift is detected, corresponding to the presence of ice on the surface. Step 40 is then invoked, wherein the presence of ice on the surface is indicated, in any desired format.

The simplest method for determining whether the midpoint wavelength M is greater or less than the threshold wavelength T is to compute a dimensionless decision function directly from the measured reflectance values and then compare the output of that decision function to one or more dimensionless numerical ranges. Specifically, one can compute the reflectance slope between wavelengths a and b of the step S (shown in FIG. 1), compute the reflectance slope between wavelengths b and c of the step S, and finally, compute the absolute value of the ratio of these two slopes. Such a computation is functionally and monotonically related to a determination of the midpoint wavelength of the transition, whereby a small slope ratio is equivalent to a larger (i.e., longer) midpoint wavelength and a large slope ratio is equivalent to a smaller (i.e., shorter) midpoint wavelength. A method incorporating such a computation is shown in FIG. 3 and discussed herein, but of course, other methods for calculating the midpoint wavelength M are possible and are considered within the spirit and scope of the present invention.

Figure 3:
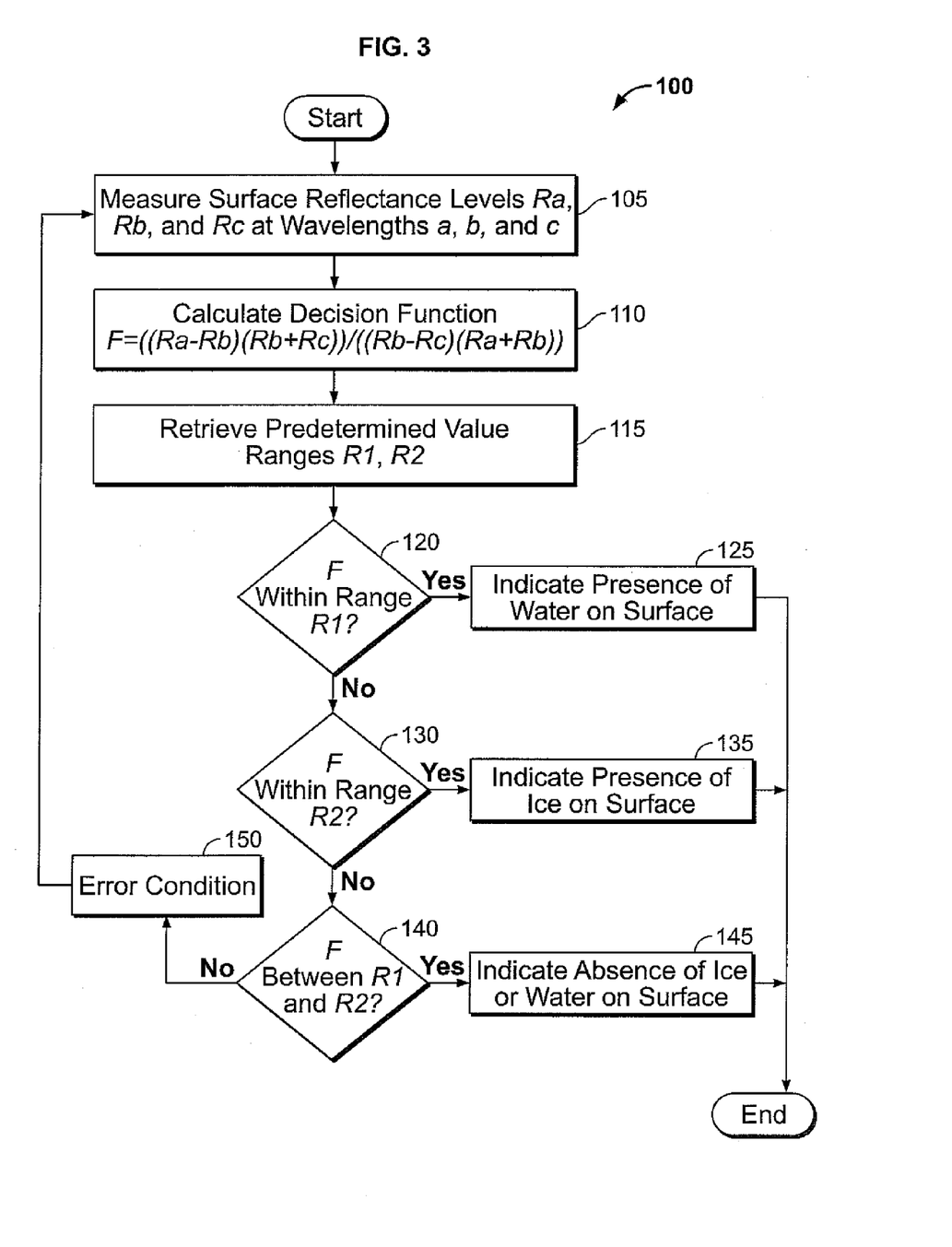
FIG. 3 is a flowchart showing another method according to the present invention for determining the presence of water or ice on a surface.

FIG. 3 is a flowchart showing another method according to the present invention, indicated generally at 100, for determining the presence or absence of liquid water or ice on a surface. The method 100 measures three distinct reflectance levels Ra, Rb, and Rc at three wavelengths a, b, and c in the vicinity of 1.4 μm in the near-infrared spectral region, applies a dimensionless decision function F to the reflectance levels, and compares the output of the decision function F to pre-defined ranges to determine the presence or absence of ice or liquid water on a surface. The ranges and the decision threshold value that separates them may be generated from a set of experimental reflectance measurements by numerical computation of the described slope ratios from each measurement, followed by statistical analysis of the set of slope ratios to determine the proper decision threshold value to obtain the desired values of detection probability and error probability. Examples of such threshold determination methods can be found in the relevant statistical pattern recognition literature.

Beginning in step 105, reflectance levels Ra, Rb, and Rc are measured from a surface at wavelengths a, b, and c. Preferably, the wavelengths a, b, and c correspond approximately to 1.3, 1.4, and 1.5 micrometers, respectively. For both liquid water and ice, the reflectance levels will be relatively larger at wavelengths shorter than 1.3 μm, and relatively smaller at wavelengths longer than 1.5 μm. Of course, any number of reflectance levels greater than one could be measured at any desired wavelengths without departing from the spirit and scope of the present invention.

It should be noted that an improved detection threshold may be determined by accounting for any shifts in the midpoint wavelength attributable to ambient or surface temperature variations, or changes in ambient light levels detected by the detector utilized with the present invention. Further, increases in the thickness of liquid water or ice coatings that cause a shift in the transitional wavelength towards shorter wavelengths can be compensated for, as well as shifts in the transitional wavelengths towards longer wavelengths due to decreases in the temperature of the liquid water or ice coating. The most difficult case for discriminating between liquid water and ice occurs for thin layers at temperatures close to zero degrees Celsius. For the case of a layer approximately 0.5 μm thick at a temperature near zero degrees Celsius, the difference in transitional wavelengths between ice and liquid water is approximately 40 nm. This difference is readily detected by the present invention.

In step 110, a dimensionless decision function F is applied to the measured reflectance levels $R_a$, $R_b$, and $R_c$. The function F is based upon known statistical classification methods, and, in its simplest form, can be expressed as follows, where F is understood to be an absolute value:

$$F = \frac{(R_a - R_b)*(R_b + R_c)}{(R_b - R_c)*(R_a + R_b)} \quad (1)$$

Preferably, the specific wavelengths a, b, and c correspond to a=1.30 μm+/−0.04 μm, b=1.40 μm+/−0.04 μm, and c=1.50 μm+/−0.04 μm, but other values could be substituted. For example, reflectance levels can be measured at wavelengths a, b, and c, wherein a=1.30 microns+0.04 microns/−0.2 microns; b=1.40 microns+/−0.05 microns, and c=1.50 microns+0.2 microns/−0.05 microns. Alternatively, the wavelengths a=1.30 microns+/−0.2 microns; b=1.40 microns+/−0.02 microns; and c=1.50 microns+/−0.02 microns could be utilized. Further, the wavelengths a=1.30 microns+/−0.02 microns; b=1.38 microns+/−0.03 microns; and c=1.45 microns+0.1 microns/−0.02 microns could be utilized.

Each $R_x$ value is computed by converting the measured light intensity data into reflectance by correcting for the instrumental transfer function, including light source spectrum and the spectral response of the lenses, filters, and camera utilized with the present invention. A finite system bandwidth about a, b, and c is assumed, and is approximately 5 nm to 50 nm in the case of a broadband light source and less than 5 nm in the case of laser sources. The decision function F could be substituted with any other suitable statistical pattern recognition or pattern classification method known in the art. Examples of such methods are set forth in standard texts such as Duda, et al., "Pattern Classification" ($2^{nd}$ Edition), Wiley—Interscience, 2000. Any other such methods can be used and are considered within the spirit and scope of the present invention.

The decision function set forth in Equation 1, above, is a monotonic function of the midpoint wavelength of the O—H absorption band edge near 1.4 μm. Output of this function is then analyzed to determine the presence or absence of liquid water or ice on a surface. In step 115, pre-determined value ranges R1 and R2 are retrieved. Range R1 stores values that correspond to the presence of liquid water on a surface, and range R2 stores values that correspond to the presence of ice on a surface. Both R1 and R2 can vary according to ice or liquid water thicknesses, ambient or surface temperatures, as well as the specific bandwidths and wavelengths analyzed. For the case of bandwidths of 5 to 20 nanometers and wavelengths a=1.30 microns, b=1.40 microns, and c=1.50 microns, range R2 will typically contain values from approximately 0.25-2.5 for thin layers of ice, and range R1 will typically contain values of approximately greater than 10 for thin layers of liquid water. Additionally, for the case of bandwidths of 5 to 20 nanometers and wavelengths a=1.300 microns, b=1.357 microns, and c=1.450 microns, range R2 will contain values of approximately 0.025-0.10 for thin layers of ice, and range R1 will contain values of approximately 1.0 to 10 for thin layers of liquid water. As can be readily appreciated, any range of values can be stored in ranges R1 and R2, depending upon varying conditions.

In step 120, a determination is made as to whether F is within the range R1, thereby indicating the presence of liquid water on the surface. If a positive determination is made, step 125 is invoked, wherein an indication is generated that liquid water is present on the surface. If a negative determination is made, step 130 is invoked.

In step 130, a determination is made as to whether F is within the range R2, thereby indicating the presence of ice on the surface. If a positive determination is made, step 135 is invoked, wherein an indication is generated that ice is present on the surface, the indication being in any desired format. If a negative determination is made, step 140 is invoked.

In step 140, a determination is made as to whether F falls between range R1 and range R2. If a positive determination is made, step 145 is invoked, wherein an indication is generated, in any desired format, that water and ice are absent from the surface. If a negative determination is made, step 150 is invoked, wherein an error condition is detected. Then, step 105 is re-invoked, so that additional measurements can be made.

The outputs generated by steps 125, 135, and 145 can be any type of audio, visual, textual, or other type of indication readily appreciable by a user. For example, a device could be provided having an audio (buzzer, speaker, etc.) or visual (LCD display, LEDs, etc.) output for indicating the presence or absence of liquid water or ice on the surface under test. Moreover, the output could be fed to an external computer for further processing and analysis, and could be remotely transmitted over a network for remote access and analysis. Additionally, the outputs could be integrated with an aircraft avionics system or automobile data bus for providing feedback to operators of such vehicles. Any conceivable means for conveying results of processing generated by the methods 10 and 100 of the present invention are considered within the spirit and scope of the present invention. Further, although sample values have been disclosed herein for the wavelengths a, b, and c, such values and transmission bandwidths associated therewith may vary. As long as sufficient light energy is available to overcome detector noise and unwanted background signals, a narrower bandwidth may be preferable to a broader one.

The methods discussed earlier and shown in FIGS. 2 and 3 can be programmed into any suitable computer system, and stored in any suitable data storage medium, such as an EEPROM or flash memory chip. Of course, other data storage media can be applied without departing from the spirit or scope of the present invention. An example of a system incorporating the methods of the present invention is illustrated with reference to FIG. 4.

Figure 4:
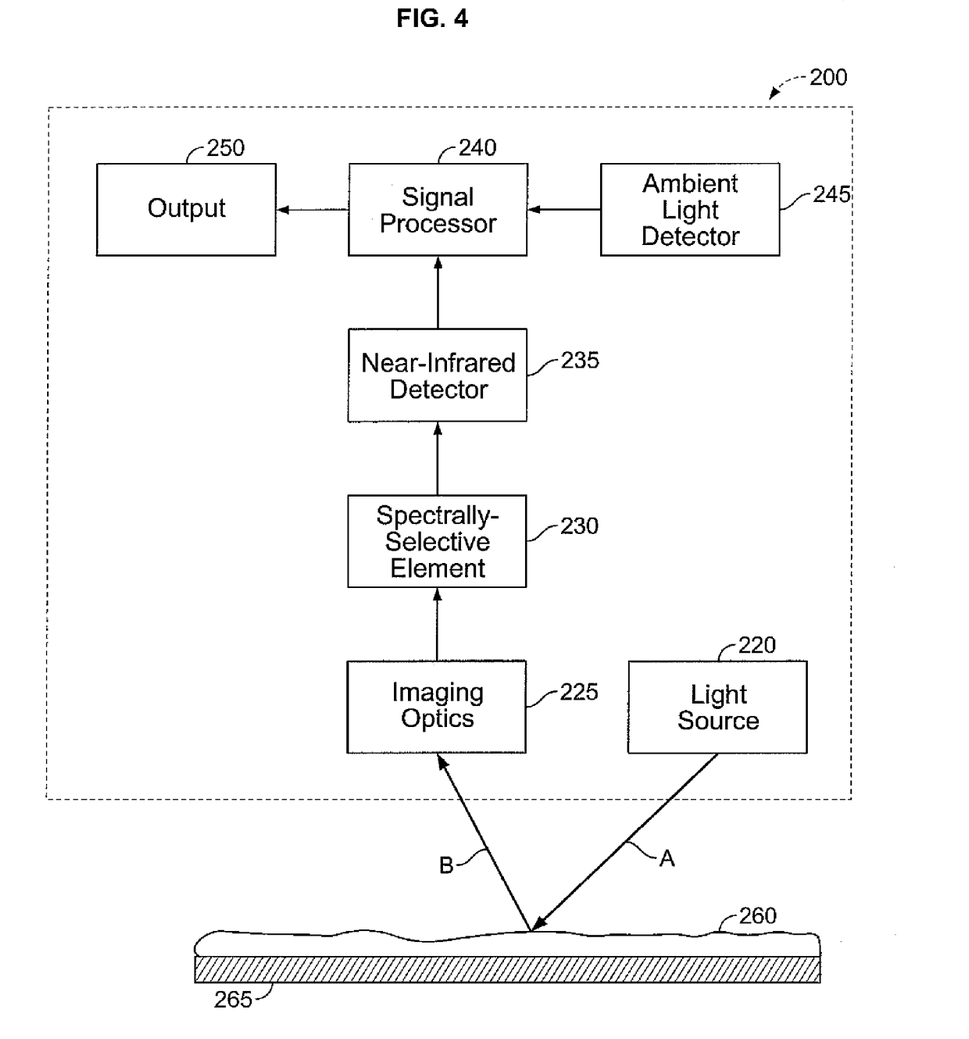
FIG. 4 is a block diagram showing a sample system for determining the presence or absence of water or ice on a surface, and incorporating one or more of the methods of the present invention.

FIG. 4 is a block diagram of a sample detection apparatus incorporating one or more of the methods of the present invention and indicated generally at 200. The detector 200 comprises a light source 220, imaging optics 225, spectrally-selective element 230, near-infrared detector 235, a signal processor 240, and an ambient light detector 245. Light A from the light source 220 is projected at a surface 265. Ice or liquid water 260 present on the surface 265 reflects the light away from the surface 265, whereupon the reflected light B is received by imaging optics 225. If no ice or liquid water 260 is present on the surface 265, the light A is reflected by the surface 265, and the reflected light is received by the imaging optics 225. The surface 265 could be any surface where ice or liquid water accumulates, including, but not limited to, aircraft surfaces (e.g., wing surfaces), runways, roadways, buildings, and other surfaces.

Light source 220 provides illumination of the surface 265, on which ice or liquid water 260 may be present. Light source 220 could be an electrically-powered light source, such as a filtered or unfiltered incandescent light, a laser or group of lasers, an array of LEDs, or other source. Further, light source 220 could be a naturally-occurring source of light, such as sunlight. Imaging optics 225 comprises a camera lens operative in the near-infrared spectral region. The optics 225 focuses an image of the surface 260 through the spectrally-selective element 230, and onto a focal plane of the near-infrared detector 235.

In a preferred embodiment of the present invention, spectrally-selective element 230 comprises three bandpass interference filters mounted on a motorized filter wheel, with bandwidths of approximately 10 to 50 nm. The three filters are centered on wavelengths a, b, and c, where a is approximately 1.3 µm+/−0.04 µm, b is approximately 1.4 µm+/−0.04 µm, and c is approximately 1.5 µm+/−0.04 µm. Less than three filters can be used, and two wavelengths can be determined. Alternatively, more than three filters and wavelengths can be utilized. As each of the filters is positioned between the imaging optics 225 and the near infrared detector 235, light having different wavelengths is passed to the detector 235. This enables the detector 235 to analyze the reflected light B at a variety of wavelengths. Of course, the spectrally-selective element 230 need not be limited to a motorized filter wheel arrangement. Indeed, any suitable spectrally-selective element could be substituted without departing from the spirit or scope of the present invention.

Light passing through the filters is passed to near-infrared detector 235. Preferably, the near-infrared detector 235 comprises an optical detector sensitive to wavelengths of from approximately 1.3 µm to 1.5 µm. The detector 235 could be any near-infrared detector known in the art, such as an InGaAs focal plane array camera, PbS vidicon, or other suitable detector. Additionally, for applications such as the automated monitoring of road surfaces, a single element detector could be used for detector 235. Light detected by the near-infrared detector 235 is converted to an electrical signal that is received by signal processor 240. The signal processor 240 also receives signals corresponding to ambient light levels that are detected by ambient light detector 245. The signal processor 240 compensates for ambient light by subtracting the ambient light levels measured by ambient light level detector 245 from the image data acquired by the near-infrared detector 235.

The signal processor 240 comprises a computer system that digitizes image data from the near-infrared detector 235 and processes same to determine whether ice or liquid water is present on the surface 265. The signal processor 240 could be any type of computer system, such as a personal computer (PC), laptop computer, embedded microprocessor, programmable logic device (PLD), application-specific integrated circuit (ASIC), digital signal processor (DSP), or any other suitable type of processor known in the art. The signal processor 240 contains one or more of the methods of the present invention, discussed earlier, that determine the presence or absence of liquid water or ice on the surface 265.

Output 250 from the signal processor 240 comprises one or more indications of the presence or absence of ice or liquid water on the surface 265. The output can be utilized to actuate one or more audio or visual indicators (e.g., one or more LEDs, lights, or sonic alerts for indicating the presence of ice or liquid water on the surface). Further, the output can be fed to a separate computer system for further review and processing. Additionally, it is conceivable that the output 250 of the signal processor 240 could be networked via a controller area network (CAN), local area network (LAN), wide area network (WAN), or other network such as the Internet, so that information acquired by the detector 200 can be accessed from remote locations. Moreover, the detector 200 could be connected to one or more device networks within an aircraft, automobile, or other vehicle, and data generated thereby can be displayed within the vehicle and appropriate responsive measures initiated.

Having thus described the invention in detail, it is to be understood that the foregoing description is not intended to limit the spirit and scope thereof. What is desired to be protected by Letters Patent is set forth in the appended claims.

What is claimed is:

1. A method for detecting ice on a surface comprising:
   acquiring a reflectance spectrum of light reflected off of a surface to be tested;
   calculating a midpoint wavelength of a transition in the reflectance spectrum;
   comparing the midpoint wavelength to a decision threshold wavelength; and
   indicating the presence of ice on the surface if the midpoint wavelength is greater than the decision threshold wavelength.

2. The method of claim 1, wherein the step of acquiring the reflectance spectrum comprises detecting reflected light off of the surface with a near-infrared camera.

3. The method of claim 2, wherein the step of acquiring the reflectance spectrum comprises detecting reflectance levels at three wavelength bands.

4. The method of claim 3, wherein the three wavelength bands are centered at approximately 1.3 microns, 1.4 microns, and 1.5 microns.

5. The method of claim 3, wherein the three wavelength bands have center wavelengths and bandwidths of 1.30 microns+/−0.04 microns, 1.4 microns+/−0.04 microns, and 1.5 microns+/−0.04 microns, respectively.

6. The method of claim 3, wherein the three wavelengths have center wavelengths and bandwidths of 1.30 microns+0.04 microns/−0.20 microns, 1.40 microns+/−0.05 microns, and 1.5 microns+0.20 microns/−0.05 microns, respectively.

7. The method of claim 3, wherein the three wavelengths have center wavelengths and bandwidths of 1.30 microns+/−0.02 microns, 1.40 microns+/−0.02 microns, and 1.50 microns+/−0.02 microns, respectively.

8. The method of claim 3, wherein the three wavelengths have center wavelengths and bandwidths of 1.30 microns+/−0.02 microns, 1.38 microns+/−0.03 microns, and 1.45 microns+0.1 microns/−0.02 microns, respectively.

9. The method of claim 1, wherein the step of comparing the midpoint wavelength to the decision threshold wavelength comprises comparing the midpoint wavelength to a decision threshold wavelength of 1.4 micrometers.

10. The method of claim 1, wherein the step of calculating the midpoint wavelength of the transition comprises applying a decision function to reflectance levels of the reflectance spectrum to obtain a dimensionless number corresponding to the midpoint wavelength.

11. The method of claim 10, wherein the decision function is:

$$F = \frac{(R_a - R_b)*(R_b + R_c)}{(R_b - R_c)*(R_a + R_b)}$$

wherein Ra, Rb, and Rc are three reflectance levels measured at three wavelengths a, b, and c, and F represents an absolute value.

12. The method of claim 10, wherein the step of comparing the midpoint wavelength to the decision threshold wavelength comprises comparing output of the decision function to a predetermined range.

13. The method of claim 12, wherein the pre-determined range is approximately 0.25-2.5 for bandwidths of 5 to 20 nanometers and center wavelengths of 1.30 microns, 1.40 microns, and 1.50 microns, respectively.

14. The method of claim 12, wherein the pre-determined range is approximately 0.025-0.10 for bandwidths of 5 to 20 nanometers and center wavelengths of 1.300 microns, 1.357 microns, and 1.450 microns, respectively.

15. The method of claim 12, further comprising indicating the presence of ice on the surface when the midpoint wavelength falls within the predetermined range.

16. The method of claim 1, wherein the step of indicating the presence of ice on the surface comprises generating an audio or visual indication of the presence of ice on the surface.

17. A method for detecting liquid water on a surface comprising:
    acquiring a reflectance spectrum of light reflected off of a surface to be tested;
    calculating a midpoint wavelength of a transition in the reflectance spectrum;
    comparing the midpoint wavelength to a decision threshold wavelength; and
    indicating the presence of liquid water on the surface if the midpoint wavelength is less than the decision threshold wavelength.

18. The method of claim 17, wherein the step of acquiring the reflectance spectrum comprises detecting light reflected off of the surface with a near-infrared camera.

19. The method of claim 18, wherein the step of acquiring the reflectance spectrum comprises detecting reflectance levels in three wavelength bands.

20. The method of claim 19, wherein the three wavelength bands are centered at approximately 1.3 microns, 1.4 microns, and 1.5 microns.

21. The method of claim 19, wherein the three wavelength bands have center wavelengths and bandwidths of 1.30 microns+/−0.04 microns, 1.4 microns+/−0.04 microns, and 1.5 microns+/−0.04 microns, respectively.

22. The method of claim 19, wherein the three wavelength bands have center wavelengths and bandwidths of 1.30 microns+0.04 microns/−0.20 microns, 1.40 microns+/−0.05 microns, and 1.5 microns+0.20 microns/−0.05 microns, respectively.

23. The method of claim 19, wherein the three wavelength bands have center wavelengths and bandwidths of 1.30 microns+/−0.02 microns, 1.40 microns+/−0.02 microns, and 1.50 microns+/−0.02 microns, respectively.

24. The method of claim 19, wherein the three wavelength bands have center wavelengths and bandwidths of 1.30 microns+/−0.02 microns, 1.38 microns+/−0.03 microns, and 1.45 microns+0.1 microns/−0.02 microns, respectively.

25. The method of claim 17, wherein the step of comparing the midpoint wavelength to the decision threshold wavelength comprises comparing the midpoint wavelength to a decision threshold wavelength of 1.4 micrometers.

26. The method of claim 17, wherein the step of calculating the midpoint wavelength of the transition comprises applying a decision function to reflectance levels of the reflectance spectrum to obtain a dimensionless number corresponding to the midpoint wavelength.

27. The method of claim 26, wherein the decision function is:

$$F = \frac{(R_a - R_b)*(R_b + R_c)}{(R_b - R_c)*(R_a + R_b)}$$

wherein Ra, Rb, and Rc are three reflectance levels measured at three wavelengths a, b, and c, and F represents an absolute value.

28. The method of claim 26, wherein the step of comparing the midpoint wavelength to the decision function wavelength comprises comparing output of the decision function to a predetermined range.

29. The method of claim 28, wherein the pre-determined range is at least 10 for bandwidths of 5 to 20 nanometers and wavelengths of 1.30 microns, 1.40 microns, and 1.50 microns, respectively.

30. The method of claim 28, wherein the pre-determined range is 1.0-10 for bandwidths of 5 to 20 nanometers and wavelengths of 1.300 microns, 1.357 microns, and 1.450 microns, respectively.

31. The method of claim 28, further comprising indicating the presence of liquid water on the surface when the midpoint wavelength falls within the predetermined range.

32. The method of claim 17, wherein the step of indicating the presence of liquid water on the surface comprises generating an audio or visual indication of the presence of liquid water on the surface.

33. A method for detecting whether ice or liquid water is present on a surface comprising:
    measuring three reflectance levels of light reflected off of a surface in three wavelength bands;

calculating a midpoint wavelength of a transition using the three reflectance levels;

indicating the presence of ice on the surface if output of the decision function falls within a first pre-determined range; and indicating the presence of liquid water on the surface if output of the decision function falls within a second pre-determined range.

34. The method of claim 33, wherein the step of measuring the reflectance levels comprises detecting reflected light off of the surface with a near-infrared camera.

35. The method of claim 33, wherein the three wavelength bands are centered at approximately 1.3 microns, 1.4 microns, and 1.5 microns.

36. The method of claim 33, wherein the three wavelength bands have center wavelengths and bandwidths of 1.30 microns+/−0.04 microns, 1.4 microns+/−0.04 microns, and 1.5 microns+/−0.04 microns, respectively.

37. The method of claim 33, wherein the three wavelength bands have center wavelengths and bandwidths of 1.30 microns+0.04 microns/−0.20 microns, 1.40 microns+/−0.05 microns, and 1.5 microns+0.20 microns/−0.05 microns, respectively.

38. The method of claim 33, wherein the three wavelength bands have center wavelengths and bandwidths of 1.30 microns+/−0.02 microns, 1.40 microns+/−0.02 microns, and 1.50 microns+/−0.02 microns, respectively.

39. The method of claim 33, wherein the three wavelength bands have center wavelengths and bandwidths of 1.30 microns+/−0.02 microns, 1.38 microns+/−0.03 microns, and 1.45 microns+0.1 microns/−0.02 microns, respectively.

40. The method of claim 33, further comprising measuring reflectance levels in four or more wavelength bands.

41. The method of claim 33, wherein the step of calculating the midpoint wavelength of the transition comprises applying a decision function to the three reflectance levels to obtain a dimensionless number corresponding to the midpoint wavelength.

42. The method of claim 41, wherein the decision function is:

$$F = \frac{(R_a - R_b) * (R_b + R_c)}{(R_b - R_c) * (R_a + R_b)}$$

wherein Ra, Rb, and Rc are three reflectance levels measured at three wavelengths a, b, and c, and F represents an absolute value.

43. The method of claim 33, wherein the first pre-determined range is approximately 0.25-2.5 for bandwidths of 5 to 20 nanometers and center wavelengths of 1.30 microns, 1.40 microns, and 1.50 microns, respectively.

44. The method of claim 33, wherein the first pre-determined range is approximately 0.025-0.10 for bandwidths of 5 to 20 nanometers and center wavelengths of 1.300 microns, 1.357 microns, and 1.450 microns, respectively.

45. The method of claim 33, wherein the second pre-determined range is at least 10 for bandwidths of 5 to 20 nanometers and center wavelengths of 1.30 microns, 1.40 microns, and 1.50 microns, respectively.

46. The method of claim 33, wherein the second pre-determined range is approximately 1.0-10 for bandwidths of 5 to 20 nanometers and center wavelengths of 1.300 microns, 1.357 microns, and 1.450 microns, respectively.

47. The method of claim 33, further comprising indicating the absence of ice and liquid water on the surface when the output of the decision function falls between the first and second predetermined ranges.

48. An apparatus for detecting the presence of ice or liquid water on a surface comprising:

a light source for illuminating a surface to be tested;

a detector for detecting at least three reflectance levels Ra, Rb, and Rc at three wavelengths a, b, and c; and a signal processor having a decision function for calculating a midpoint wavelength of a reflectance spectrum based upon the at least three reflectance levels Ra, Rb, and Rc and determining the presence of ice or water using the midpoint wavelength.

49. The apparatus of claim 48, wherein the light source comprises one of an incandescent light, a laser, an LED, or sunlight.

50. The apparatus of claim 48, wherein the detector comprises one of a near-infrared detector, an infrared camera, an InGaAs focal-plane array, or a PbS vidicon.

51. The apparatus of claim 48, further comprising a spectrally-selective element for measuring the at least three reflectance levels.

52. The apparatus of claim 48, wherein the signal processor indicates the presence of ice on the surface when the midpoint wavelength falls within a first predetermined range.

53. The apparatus of claim 52, wherein the signal processor indicates the presence of liquid water on the surface when the midpoint wavelength falls within a second predetermined range.

54. The apparatus of claim 53, wherein the signal processor indicates the absence of ice and water on the surface when the midpoint wavelength falls between the first and second predetermined ranges.

55. The apparatus of claim 48, wherein the decision function is:

$$F = \frac{(R_b - R_c) * (R_a + R_b)}{(R_b + R_c) * (R_a - R_b)}$$

where F represents an absolute value.

56. The apparatus of claim 48, further comprising an ambient light detector connected to the signal processor for measuring ambient light levels.

* * * * *